United States Patent [19]

Fiege et al.

[11] 4,113,975
[45] Sep. 12, 1978

[54] PROCESS FOR PURIFYING ALKYLPHENOLZ

[75] Inventors: Helmut Fiege; Josef Haydn; Johann Renner, all of Leverkusen; Karlfried Wedemeyer, Cologne, all of Germany

[73] Assignee: Bayer Aktiengesellschaft, Leverkusen, Germany

[21] Appl. No.: 757,422

[22] Filed: Jan. 6, 1977

[30] Foreign Application Priority Data

Jan. 21, 1976 [DE] Fed. Rep. of Germany ....... 2602149

[51] Int. Cl.$^2$ ............................................. C07C 37/28
[52] U.S. Cl. ..................................... 568/756; 568/759
[58] Field of Search ........... 260/621 A, 621 B, 624 A, 260/627 R, 627 G

[56] References Cited

U.S. PATENT DOCUMENTS

| 2,493,781 | 1/1950 | Schneider et al. | 260/624 A |
| 2,656,312 | 10/1953 | Stevens et al. | 260/624 A |
| 2,714,087 | 7/1955 | Stevens et al. | 260/624 A |

FOREIGN PATENT DOCUMENTS

| 2,215,452 | 11/1972 | Fed. Rep. of Germany | 260/621 A |
| 557,519 | 11/1972 | United Kingdom | 260/624 A |
| 582,057 | 11/1946 | United Kingdom | 260/621 A |

OTHER PUBLICATIONS

Weinrich, "Ind. & Eng. Chem.", vol. 35, (1943), pp. 264–272.

*Primary Examiner*—Bernard Helfin
*Assistant Examiner*—Werren B. Lone
*Attorney, Agent, or Firm*—Burgess, Dinklage & Sprung

[57] ABSTRACT

A process for the removal of acids and potential acid-forming agents from a composition containing such acids and potential acid-forming agents and an alkylphenol which composition is obtained by reacting phenols with alkenes in the presence of sulfuric acid or a sulfonic acid, and for treating the effluent thereby obtained, the process being characterized by the steps of:

(a) extracting a major amount of the acid constituents from the alkylphenol mixture by means of water;

(b) treating the alkylphenol mixture with a dilute aqueous alkali solution in an amount such that the alkali is insufficient to neutralize all the acid originally present in the alkylphenol mixture, (c) separating the alkylphenol mixture from the aqueous alkali solution;

(d) combining the aqueous phases obtained from steps (a) and (b);

(e) heating the combined aqueous phases to a temperature of 100° to 200° C, (f) separating off the organic phase obtained in step (e); and (g) discharging the aqueous phase.

16 Claims, 5 Drawing Figures

PROCESS FOR PURIFYING ALKYLPHENOLZ

BACKGROUND OF THE INVENTION

1. Field of the Invention

The invention relates to a process for purifying alkylphenols obtained by alkylation of phenols in the presence of acid catalysts and to the treatment of the effluent thus obtained.

In the text which follows the alkylphenols and butylphenols obtained from the alkylation, and in particular butylation, of phenols are termed the alkylate and butylate.

2. Discussion of Prior Art

Sulphuric acid is customarily used as the catalyst for the alkylation of phenols, especially of cresols, with isobutene (Ind. Chem. Engng. Volume 35 (1943), page 266). Oleum or phenolsulphonic acids (British patent specification No. 701,438) or $SO_3$ (DOS (German Published Specification) No. 2,215,452) can also be used.

When the alkylation reaction has ended, the acid catalyst contained in the alkylate must be rendered inactive and/or removed. Usually this is effected by means of a treatment with aqueous sodium hydroxide solution or sodium carbonate solution (DT-AS (German Published Specification) No. 1,145,629 and Ind. Chem. Engng., loc cit., page 269).

The treatment with alkali must be carried out very intensively. If this is not the case it is possible, according to our own experience, for substances which have an acid action to form from potential acid-forming agents during storage of the alkylate or at the high temperatures which are required for the distillation, which substances, in the case of tert.-butyl cresols, lead to the tertiary butyl group being split off again, thereby rendering distillation of the alkylate impossible. However, whether or not a total process comprising further steps can be carried out can depend on whether or not the alkylate can be distilled. This is the case, for example, for the fractionation of di-tert.-butyl cresols, which is of great industrial importance for the separation of mixtures of m-cresol and p-cresol (Ind. Engng. Chem., loc cit., page 271 and Franck, Collin, Steinkohlenteer (Coal Tar) Springer Verlag 1968, page 82).

The removal of the acid and of the acid-forming compounds is effected, for example, by circulating the crude butylate mixture together with an excess of a 5 to 7 per cent strength by weight aqueous solution of an alkali metal hydroxide several 100 times under a pressure of 5 bars, at about 120° C and with an average residence time of 40 minutes. After the aqueous alkali solution has separated out, considerable amounts of water are still dissolved or emulsified in the butylate phase and the latter thus also contains considerable amounts (about 1 per cent by weight) of the readily water-soluble alkali metal cresol-sulphonates, as can be seen from Table III (loc., page 272). Furthermore, alkali, which is necessary to ensure that the crude butylate mixture is stable on distillation, is dissolved in the butylate. On distillation, that is to say after the aqueous phase has been separated off, alkali metal cresol-sulphonates, in the main, separate out in the butylate and can lead to considerable breakdowns in operation, especially in the case of continuous distillations. In every case these products, which give a tar-like residue, have an adverse effect, both because of their amount and because of their properties, on the working up, by distillation, of the crude alkylate mixture and there is a direct relationship between the sulphur content, and thus the alkali metal sulphonate content, of the alkylate mixture and its decreasing stability to distillation (Ind. Engng. Chem., loc. cit., page 271).

In order further to remove the alkali metal sulphonates, it has already been proposed to rinse several times with a large amount of water, after the wash with alkali (British patent specification No. 701,438; DT-OS (German Published Specification) No. 2,215,452). However, the low residual alkalinity which is necessary to ensure stability on distillation is also eliminated in this way and the amount of effluent is greatly increased.

The washings, which have an alkaline reaction, represent a particular problem in the process according to the state of the art. They contain, in solution, the sulphonic acids, in the form of the alkali metal salts, in addition to phenols and alkylphenols. However, whilst the dissolved phenols and alkylphenols, in particular the cresols and butyl cresols, can be recovered, at least in part, for example by an extraction with benzene (Ind. Engng. Chem. Volume 35 (1943), page 271), this is not possible in the case of the alkali metal sulphonates, in which several per cent by weight of the valuable starting material, that is to say cresol, are bound and which represent the main impurity in the effluent. Elimination of the effluent is also difficult since, as is known, the alkali metal sulphonates cannot be precipitated with calcium oxide in the form of a suspension of calcium hydroxide, the salts which remain on evaporation of the wash waters can not be dumped because of their ready solubility in water and combustion of the effluent is also problematical because of the evolution of sulphur dioxide associated therewith.

The purification of the butylate mixture obtained represents a largely unsolved part of the problem, especially in the case of the industrial process for the butylation of cresols, as part of the separation of mixtures of m-cresol and p-cresol.

OBJECTS OF THE INVENTION

It is clearly desirable to have a process in which acids are as far as possible removed from the alkylate mixture, the potential acid-forming agents are reliably rendered inactive, a small amount of alkali metal hydroxide solution is consumed, a small amount of effluent is formed, the effluent can be worked up with recovery of the valuable substances contained therein and the effluent can be eliminated without pollution of the environment.

SUMMARY OF THE INVENTION

A process for removing acids and potential acid-forming agents from the alkylphenol mixture obtained by reacting phenols with alkenes in the presence of sulphuric acid or sulphonic acids and for treatment of the effluent thus obtained has now been found, in which (a) the bulk of the acid constituents are extracted from the resulting alkylphenol mixture by means of water, (b) the alkylphenol mixture is then treated with a dilute aqueous solution of alkali in an amount such that it is not sufficient to neutralise all of the acid originally contained in the alkylphenol mixture, and (c) the alkylphenol mixture is then further processed in the customary manner, whilst (d) the aqueous phases obtained in steps (a) and (b) are combined and (e) heated to a temperature of 100° to 200° C and (f) the organic phase thus obtained is then separated off and (g) if necessary after further treatment, the aqueous phase is discharged as effluent in a known manner.

BRIEF DESCRIPTION OF DRAWINGS

Referring to the drawings herein.

DESCRIPTION OF SPECIFIC EMBODIMENTS

Figure 1:
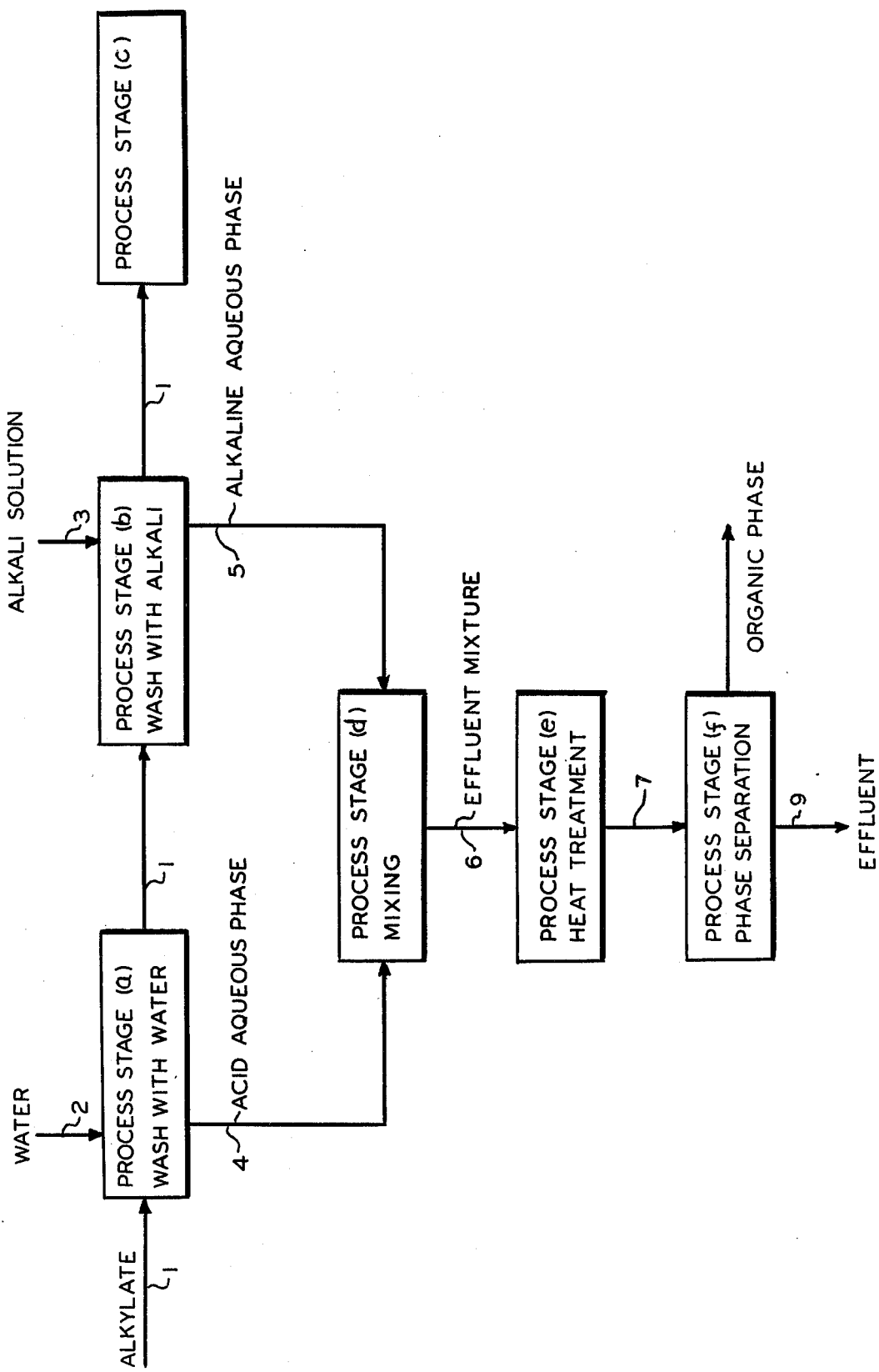
FIG. 1 is a schematic drawing showing a process for carrying out the invention.

The process according to the invention can be illustrated by FIG. 1, which follows.

The preferred acid catalyst used for the alkylation is sulphuric acid, oleum or $SO_3$, and is present, in the crude mixture obtained from the alkylation, largely in the form of various phenolsulphonic acids and, in the case of the butylation of cresol, for example, is present in the form of cresol-, mono-tert.-butyl cresol- and di-tert.-butyl cresol-sulphonic acids. The total acid content in the alkylate can be determined, for example, by potentiometric titration with 0.1 N alkali metal hydroxide solution. The acidity of the alkylate mixture obtained depends on the amount of sulphuric acid, or of equivalent compounds, previously employed. Usually, acidities of less than 0.25 equivalent of $H^+$/kg of alkylate are to be expected and an acidity of 0.1 equivalent of $H^+$/kg signifies that 1 kg of alkylate contains about 25 g of sulphonic acids.

In the process according to the invention, the acids contained in the crude alkylate should already be washed out to the greatest possible extent with water. In general, the residual acidity after the wash with water should be only 0.005 equivalent of $H^+$/kg of alkylate or less. Under operating conditions which are otherwise kept constant, the amount of water required for this is proportional to the initial acidity and inversely proportional to the desired residual acidity and can be easily determined by a few preliminary experiments.

In order to obtain the effluent in a small amount, and thus in a concentrated form, it is generally appropriate to effect the washing out of the acids in several stages with intermediate separation of the acid washings. According to the invention, the multi-stage wash can be carried out in cross-current, that is to say using fresh water in every stage, or, particularly advantageously, in counter-current, that is to say fresh water is used only in the final stage of the wash and in the other stages of the wash the wash water separated off is in each case employed for the subsequent stage of the wash. The total amount of effluent can be advantageously reduced in this way.

For example, in the case of a crude alkylate mixture which has an acidity of 0.100 equivalent of $H^+$/kg, at 60° C about 350 parts by weight of water are required per 100 parts by weight of alkylate in order to bring the residual acidity down to 0.003 equivalent of $H^+$/kg when only one washing stage is carried out, whilst when two washing stages are operated in cross-current about 50 parts by weight of water for each stage, that is to say a total of 100 parts by weight of water, are required per 1,000 parts by weight of alkylate and when two washing stages are operated in counter-current the amount of water required per 1,000 parts by weight of alkylate is only 50 parts by weight.

According to the invention, the wash with water (a) is followed by a wash with a dilute aqueous solution of alkali (b). During this wash, the acids which have not yet been washed out are neutralised, potential acid-forming agents are rendered inactive and a small residual alkalinity of at least 0.001 equivalent of hydroxyl ion/kg of alkylate is produced, in order to obtain an alkylate which is stable on distillation.

Aqueous solutions of alkali which can be used are, in general, aqueous solutions of alkali metal carbonates and alkali metal hydroxides, especially of the corresponding sodium and potassium compounds. The amount and concentration of these aqueous solutions of alkali can be varied within wide limits but the total amount of alkali metal hydroxide or alkali metal carbonate must be such that the effluents obtained from this wash with alkali still have a distinct alkaline reaction, that is to say have a pH value greater than 9, but after mixing with the effluents from the wash with water give an effluent mixture which has a distinct acid reaction and the pH value of which is less than 2. In general, the concentration of the solution of alkali can be less than 20, preferably 1 to 10 and especially 2 to 5,% by weight of alkali metal hydroxide or alkali metal carbonate, whilst the amount of this solution depends on the prevailing conditions in the particular case, the acidity of the alkylate and the requirements of the process according to the invention; furthermore, within these limits, other technical considerations will play a part in the choice of this solution.

In particular, it can be advantageous, for reasons of the load on the effluent, to select the amount of water employed in process stage (a) and the amount of the solution of alkali employed in process stage (b) to be as low as possible, and thus to select a correspondingly high concentration of alkali, since, corresponding to the solubility of organic compounds in water and aqueous solutions, the total amount of organic compounds in the effluent which is obtained after process stage (f) increases as the amount of the effluent increases.

It is essential that as complete as possible a removal and/or conversion of potential acid-forming agents is effected by the treatment of the alkylate with the solution of alkali (b). This can be achieved only by means of an adequate contact time between the alkylate and the solution of alkali and this time depends on the conditions prevailing in each particular case. The time is adequate when no further alkylene is eliminated from the alkylate on heating. Thus, the adequate contact time can be determined by a few experiments, for example by a test such as is described below for a butylate.

Of course, the wash with alkali (b) can also be carried out as a multi-stage wash in cross-current or counter-current, but a single stage wash with a 2 to 5 percent strength by weight solution of an alkali metal carbonate or alkali metal hydroxide at temperatures between about 40° and 100° C is generally sufficient when the contact time is adequate. It is not possible to specify a contact time which is generally adequate; this time depends, for example, on the temperature and on the pretreatment of the alkylate mixture and in a given case can be determined easily as follows. At a given temperature, the contact time of the solution of alkali with the alkylate mixture is adequate when, after distilling off the low-boiling compounds, no isobutene is eliminated from a sample of the washed alkylate on subsequent heating to 250° C for 30 minutes. At about 60° C, for example, an average contact time of about 30 minutes can be sufficient for washing 1,000 parts by weight of an alkylate mixture with 3 percent strength by weight aqueous sodium hydroxide solution. The contact time required is the shorter, the higher the temperature.

Furthermore, according to the process of the invention, the alkylate should possess a residual alkalinity of at least 0.001 equivalent of $OH^-$/kg after the wash with alkali (b); when adequate amounts of alkali are employed this requirement is frequently already met as described above, after a contact time shorter than the adequate time. However, it is essential that the stability of the alkylate to heat and over a period of time is ensured.

Both the wash with water (a) and the wash with alkali (b) can be carried out stepwise or continuously.

In general, process stages (a) and (b) are carried out under normal pressure or under the pressure which results at the selected temperature. The pressure can be up to 5, and especially up to 3, bars. Preferably, the process stages are carried out under the pressure at which the alkylphenol mixture to be purified is obtained — without intermediate letting down — from the alkylation, for example under a pressure of up to 2 bars.

Preferably, process stages (a) and (b) are carried out at temperatures between 40° and 95° C but it is also possible to work at a lower temperature and, optionally under pressure, also at a higher temperature.

If the washes (a) and (b) are carried out stepwise, it is possible to use apparatuses which can serve both as mixers and as settlers or to use special mixer/settler arrangements, such as are customary according to the state of the art.

In addition to columns which operate on the gravity principle by means of rotary inserts, pulsating liquid columns or pulsating inserts, or apparatuses which utilise centrifugal force for mixing and separating the phases, apparatuses which can be used for carrying out the washes continuously are, in particular, mixer/settler batteries. It is also possible to use different apparatuses for the wash with water and the wash with alkali. For example, it can be appropriate, because of the requisite contact time, to carry out the wash with alkali in a mixer/settler pair and to carry out the preceding wash with water in an apparatus which operates on a different principle. In each case, customary apparatuses which are known according to the state of the art can be used for the process according to the invention.

Subsequently, the acid effluents from the wash with water (a) and the alkaline effluents from the wash with alkali (b) are combined (d) and then have an acid reaction, since, according to the invention, an amount of alkali solution which is not sufficient for complete neutralisation of the total acid originally present is used in the second stage (b).

In addition to free acids, in particular sulphonic acids, the effluent mixture obtained after combination (d) also contains the alkali metal salts, especially the sodium salts, of these acids and also, in a lesser amount, dissolved proportions of the alkylate. The mixture has a very high chemical oxygen demand (COD value) and a highly unfavourable COD/BOD ratio (BOD = biological oxygen demand). According to the invention this effluent mixture is now heated, in a further process stage (e), to temperatures of about 100° to 200° C, preferably of between 140° and 190° C. In this way the sulphonic acids and their alkali metal salts are split into the phenols and sulphuric acid and/or their salts.

Since this heating is to temperatures which are above the boiling point of the effluent, it must be carried out in pressure-resistant apparatuses. Preferably, heating is carried out without external application of pressure under the pressure which results in the closed apparatus at the scission temperature selected.

The reaction time required for this effluent treatment (e) is inversely proportional to the chosen temperature; the higher the temperature, the shorter is the time required for the effluent treatment. For example, 5hours' heating to about 170° C can suffice; when the reaction temperature is raised by 10° C only about half the reaction time is required and when the reaction temperature is lowered by 10° C the reaction time must be approximately doubled. The reaction time required for virtually complete scission of the sulphonic acid in a particular case can be determined easily by a few preliminary experiments.

The heating (e), according to the invention, of the effluent mixture can be carried out stepwise or continuously, isothermally or adiabatically. When heating is carried out continuously a longer average residence time may be required than when heating is carried out stepwise. Advantageously, continuous heating can be carried out in stirred kettles, tube reactors or tower-shaped reactors which are provided with packings or inserts, or in reactor cascades.

After the heating (e), according to the invention, of the effluent mixture, the resulting organic phase, which contains the water-insoluble organic compounds which have been formed, namely phenols, such as cresols, mono-tert.-butyl cresols and di-tert.-butyl cresols, can be separated off in the customary manner. The organic phase, which is present as the upper phase, can be separated off either at elevated temperature under pressure or, after appropriate cooling, under normal pressure. The organic phase is preferably separated off at temperatures below 60° C under normal pressure.

After the organic phase has been separated off, an almost colourless dilute sulphuric acid which, although it contains alkali metal sulphates, contains virtually no further sulphonic acids and which has a COD value which is only a fraction of the original COD value, remains as the lower aqueous phase. For example, the COD value still found for an effluent, which had a COD value of 451,000 mg of $O_2$ per liter, after it had been heated to 170° C for 5 hours and cooled to room temperature and the organic phase had been separated off was, after the aqueous phase had settled well, only 21,000 mg of $O_2$ per liter. The content of sulphonic acids had fallen from an original value of more than 250 g/l to less than 0.3 g/l.

The residual COD value was essentially due to the phenols still dissolved in the aqueous phase and the amount of these phenols corresponds approximately to the distribution equilibrium of the phenols, at the corresponding temperature, between the organic phase and the aqueous phase containing sulphuric acid. The COD value of the effluent can be reduced even further by removing the dissolved phenols. This can be effected in a customary manner, for example by steam distillation, extraction with organic solvents, absorption on active charcoal or by chemical destruction by oxidation. In general, however, neutralisation of this aqueous effluent containing sulphuric acid, for example with suspended calcium hydroxide, suffices to enable it to be fed to a biological effluent treatment. In fact, it was found that the effluent, thus obtained, after neutralisation possesses no harmful action against Pseudomonas fluorescenz and that the $BOD_{10}$ value is about equal to the COD value, that is to say that a complete biological degradation of the organic substance still present in this effluent is possible.

As already mentioned, the process according to the invention can be varied to a considerable extent and this can also additionally be used in order to reduce the amount of effluent obtained, although, in itself, the amount of effluent obtained in the process according to the invention is already low. Since, as a result of the given solubilities, the total amount of organic substances contained in the effluent is proportional to the amount of water, a reduction in the amount of effluent also reduces the environmental pollution of natural waters by organic substances. However, the acid concentration and salt concentration in the effluent increases when the amount of effluent is reduced and in some cases a further treatment of the effluent, in a known manner, may be required before it is discharged, depending on whether it is discharged into an industrial main effluent sewer or a sewage treatment plant or is discharged direct into natural water. In the latter case a further neutralisation is necessary because of the acid content of the effluent; it can also be necessary to neutralise the effluent before it is discharged into a sewage treatment plant if neutralisation is not carried out in the sewage treatment plant, whilst when the effluent is discharged into an industrial main effluent sewer any further treatment can optionally be dispensed with. However, any required treatment of the aqueous phase, which is discharged as effluent after (g), is part of the state of the art.

The organic phase (f) which is separated off after the effluent has been heated (e) can advantageously be recycled into the process since it essentially consists only of compounds which are also present in the alkylate mixture employed. Since this phase can still contain small traces of acid, it is particularly advantageously recycled into process step (a) or (b). However, if necessary after a preceding distillation with the addition of alkali, it can also be fed to the starting material for the alkylation.

According to an advantageous embodiment of the process according to the invention, the acids are extracted from the crude alkylate mixture by means of water in the first stage using two or more extraction units, in particular mixer/settler pairs, which are arranged in series, and the water is fed in cross-current or, preferably, counter-current.

Figure 2:
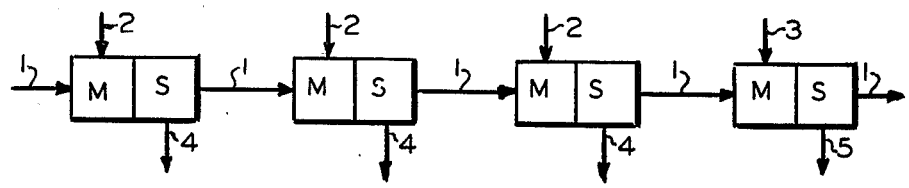
FIGS. 2 and 3 illustrate the water washing procedure involved using the cross-current principle and the counter-current principle wherein in both cases three extraction stages are employes.
Figure 3:
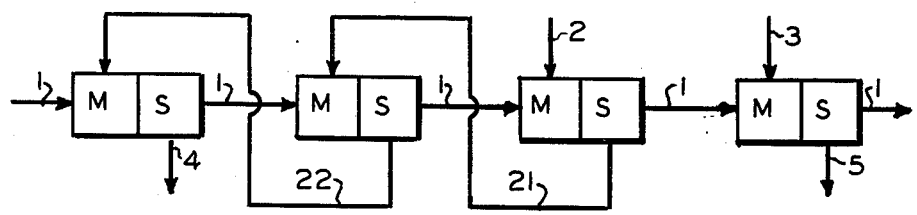

FIGS. 2 and 3 which follow are intended to illustrate the wash with water using the cross-current principle and the counter-current principle and in both cases three extraction stages for this purpose are shown diagramatically, which stages can each consist, for example, as in the diagram, of a mixer (M)/settler (S) pair. In an analogous manner the figures also show the wash with alkali (b). The arrows 1 show the flow of the alkylate, whilst 2 represents the feed for the water and 3 represents the feed for the alkali solution, 4 represents the acid effluent which flows off and 5 represents the alkaline effluent which flows off and 21 and 22 represent the water flow.

In each case the figures show only process stage (a) and (b) and the representation of the process stages (a) and (b) is diagrammatical only and given only by way of example; likewise, the number of extraction stages in process stages (a) and (b) is also given only by way of example.

Of course, it is also possible for only two or for more than three extraction stages to be used in the two variants of process stage (a).

In all the variants of the process according to the invention it is, of course, possible, when one of process stages (a) or (b) is carried out continuously in several stages, also to operate these stages in such a way that water or the alkali solution is allowed to circulate and, at each stage, only a part of the aqueous phase is withdrawn after the wash and the amounts withdrawn are replaced by fresh water or by alkali solution of the appropriate concentration.

According to a particular variant of the process of the invention, the combination (d) of the acid effluents from process stage (a) and the alkaline effluents from process stage (b), which takes place between process stages (b) and (d) can also be effected in such a way that the alkaline effluent from process stage (b) is recycled into process stage (a), in place of water. Since the alkali content of the effluent from process stage (b) is not sufficient to neutralise all the acids contained in the crude alkylate, the effluent is soon neutralised and thus corresponds to a water which contains neutral salts, such as can be used in stage (a); indeed, tap water which is customarily used for washes of this type contains neutral salts or is even slightly acid or alkaline. Advantageously, this embodiment can be used when process stage (a) is carried out by the counter-current principle in two or more extraction stages.

Figure 4:
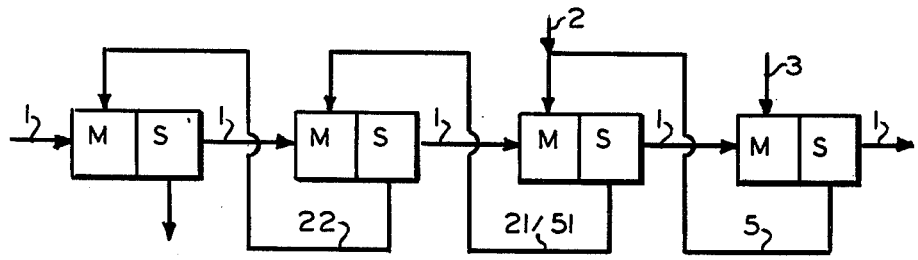
FIG. 4 is a view similar to FIGS. 2 and 3 diagramatically showing another method by which acid effluents from the process can be washed.

This is indicated diagrammatically and by way of example in FIG. 4 below with a total of four extraction stages (M,S); the arrows 1 represent the flow of the alkylate, whilst the arrow 3 indicates the feed for the alkali solution. In place of water, the alkaline effluent 5 is then fed, optionally with the addition of water 2, into process stage (a) and its subsequent flow is indicated by 21/51 and 22.

However, in the diagram it is possible only to indicate a clear separation between the process stages (a) and (b), whilst in reality the point at which the boundary between the two process stages lies and at which neutralisation of the alkali solution has taken place and, thus, mixing (d) is also effected, cannot be clearly fixed and is dependent on the conditions prevailing in a particular case.

Figure 5:
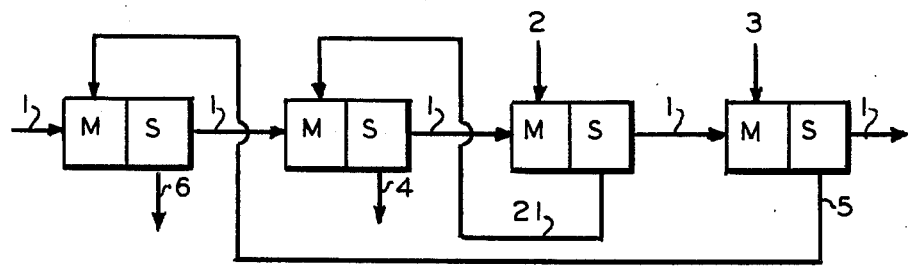
FIG. 5 is a view similar to FIGS. 2 – 4 inclusive showing diagramatically a further variant of the process for the treatment of the acid containing aqueous phases involved in the process.

FIG. 5, which follows, indicates diagrammatically a further variant of the process according to the invention, in which the alkaline effluent 5 from the wash with alkali (b) is fed, in place of water, into the first extraction stage of the wash with water (a), whilst the further extraction stages, of the wash with water (a), for which two mixer M /settler S pairs are indicated by way of example in the diagram, are operated in a separate counter-current with water. Mixing (d) takes place in the first extraction stage of the wash with water (a): the mixture of effluents 6 and the remaining acid effluent 4 are fed together into the heat treatment (e).

The technical advance achieved by the process according to the invention lies in the fact that the disadvantages, described above, of the process of the state of the art are avoided or, to express it in a positive manner, in the fact that a readily biodegradable effluent is obtained and pollution of the environment is thus prevented; furthermore, the raw materials employed and the process products are recovered as completely as possible, the consumption of auxiliaries, such as water and an alkali metal hydroxide or alkali metal carbonate, is considerably reduced and the quality of the alkylate mixture obtained is raised because the latter can be distilled with considerably greater ease.

A further advantage of the process according to the invention lies in the fact that the total amount of effluent obtained is considerably reduced in a simple manner. Since the content of organic substances in the effluent depends on their solubility, there is also a parallel substantial reduction in the total amount of organic substances, so that, as a result of this fact also, the pollution of the environment is reduced and this rduction takes place irrespective of the manner in which the effluent obtained from the process according to the invention is treated further, in a known manner, before it is fed into natural water. If the content of organic substances in the water is in itself already subject to a reduction during this subsequent treatment, the advantage of the low total amount already has an effect here inasmuch as this treatment is facilitated as a result of the lower total amount.

The process according to the invention is thus important and advantageous, in particular for carrying out the separation of the cresol by the so-called butylation of the cresol mixture and separation of the reaction product by distillation. It thus represents a considerable enrichment, compared with the state of the art.

EXAMPLE 1 a. A mixture of m-cresol and p-cresol in a ratio of 70:30, to which 2% by weight, based on cresol, of concentrated sulphuric acid was added, was butylated at 60° – 70° C in a known manner using 1.9 mols of 99% pure isobutene per mol of cresol.

b. 1,000 parts by weight of the crude alkylate obtained according to (a), which has an acidity of 0.100 equivalent of $H^+/kg$ determined by potentiometric titration with 0.1 N sodium hydroxide solution, are mixed well with 350 parts by weight of water at about 70° C. After settling, the acidity of the organic alkylate phase is then only 0.003 equivalent of $H^+/kg$ when determined in the same manner.

c. This organic phase is separated off and the mixed well with 50 parts by weight of aqueous 3 percent strength by weight sodium hydroxide solution for 20 minutes at about 60° C. After phase separation, the alkali content of the organic alkylate phase is 0.001 equivalent of $OH^-/kg$.

d. 100 g of this alkylate are heated under normal pressure in a flask which is provided with a distillation bridge and a receiver, followed by a gas meter. The low-boiling compounds distil off as the temperature rises but no isobutene is evolved even on prolonged heating (about 1.5 hours) to about 250° C.

The alkylate treated according to the invention is thus stable to heat.

EXAMPLE 2

1,000 parts by weight of the acid-containing alkylate which has an acidity of 0.100 equivalent of $H^+/kg$ and was obtained according to Example 1(a) are shaken thoroughly with twice 50 parts by weight of water at about 60° C and then once with 50 parts by weight of aqueous 2.5 percent strength by weight sodium hydroxide solution at about 70° C, shaking being carried out for 30 minutes in each case and the aqueous phase being separated off and discarded after each shaking.

The acidity of the alkylate had fallen to 0.010 equivalent of $H^+/kg$ after the first wash with water and to 0.002 equivalent of $H^+/kg$ after the second wash with water; after the wash with alkali the alkalinity of the alkylate was 0.001 equivalent of $OH^-/kg$.

Analogously to the test described in Example 1(b), this alkylate also was stable on distillation.

EXAMPLE 3 (COMPARISON EXAMPLE)

1,000 parts by weight of the alkylate which has an acidity of 0.100 equivalent of $H^+/kg$ and was obtained according to Example 1(a) were mixed well, at about 60° C, with 100 parts by weight of water. After settling, the alkylate phase was separated off and shaken thoroughly for 20 minutes at 60° C with 50 parts by weight of aqueous 3 percent strength by weight sodium hydroxide solution. After separating off the alkylate phase, potentiometric titration with 0.1 N hydrochloric acid showed an alkalinity of 0.001 equivalent of $OH^-/kg$.

A sample of this alkylate was heated as described in Example 1(b); after the low-boiling compounds had distilled off and a sump temperature of about 200° C had been reached a distinct evolution of isobutene occurred, as could be read off on the gas meter.

EXAMPLE 4

In this example an apparatus which consisted of three mixer/settler pairs arranged in series was used. Stirred kettles were used as the mixers and separating flasks were used as the settlers. Warm water circulated through the cooling jackets of the mixers and separating flasks and the internal temperature of the apparatus was maintained at 60° C by this means.

The alkylate mixture to be purified passed continuously through the battery of mixer/settlers, the flow being controlled by overflows and taking place by gravity. The average residence time of the alkylate mixture was about 10 minutes in each of the first two mixing kettles and about 25 minutes in the last mixing kettle, that is to say the wash with alkali. The average residence time of the alkylate in the separating flasks was about 10 minutes in each case.

The effluent from the second separating flasks was pumped continuously into the first mixing kettle whilst 50 parts by weight of fresh water, per 1,000 parts by weight of alkylate, were metered into the second mixing kettle. 50 parts by weight of aqueous 3 percent strength by weight sodium hydroxide solution, per 1,000 parts by weight of alkylate, were metered into the third mixing kettle.

The alkylate mixture flowing into the first mixing kettle was obtained according to Example 1(a) and had an acidity of 0.100 equivalent of $H^+/kg$.

After it had issued from the first separating flask, the alkylate had an acidity of 0.013 equivalent of $H^+/kg$ and after it had issued from the second separating flask it had an acidity of 0.003 equivalent of $H^+/kg$.

After passing through the wash with alkali, that is to say after it had issued from the final separating flask, the alkylate had an alkalinity of about 0.002 equivalent of $OH^-/kg$ and the water content was about 1 percent by weight.

The effluent which issued from the first separating flask and had a strongly acid reaction was combined with the alkaline effluent which issued from the final separating flask and about 115 parts by weight of an effluent mixture which had a strongly acid reaction were thus obtained per 1,000 parts by weight of alkylate.

EXAMPLE 5

1,000 parts by volume of the effluent mixture which was obtained according to the preceding examples and had a pH value of $\leq 1$ and a COD value of 385,000 mg of $O_2/l$ were heated to 140° C/5 bars for 10 hours in an enamel autoclave. After cooling to room temperature and settling, 120 g of an organic phase and 910 g of an aqueous phase with an acidity of 1.28 equivalents of $H^+/l$ and a COD value of 42,000 mg of $O_2/l$ were obtained.

EXAMPLE 6

1,000 parts by volume of the acid effluent mixture which was obtained according to the preceding examples and had a COD value of 384,000 mg of $O_2/l$ were heated to 155° C/6 bars for 7 hours in a glass autoclave which was fitted with a stirrer covered with Teflon. After cooling to room temperature and settling, 133 parts by weight of an organic phase and 896 parts by weight of an aqueous phase which had an acidity of 1.47 equivalents of $H^+/l$ and a COD value of 26,000 mg of $O_2/l$ and in which a cresol content of 6 g/l was determined by analysis were obtained.

EXAMPLE 7

1,000 parts by volume of the acid effluent mixture which was obtained according to Example 4 and had a COD value of 451,000 mg of $O_2/l$ and a $COD/BOD_5$ ratio of 10 : 1 were heated to 170° C/9 bars for 5 hours in an enamel stirred autoclave. After cooling and settling at 25° C, 157 parts by weight of an organic phase were separated off; this phase had the following composition, which was determined by gas chromatography: 3 parts by weight of aliphatic compounds (diisobutene, a little tert.-butanol and triisobutene), 28 percent by weight of m- and p-cresol, 59 percent by weight of mono-tert.-butyl cresols, 9 percent by weight of di-tert.-btuyl cresols and 1 percent by weight of intermediate runnings and last runnings.

883 parts by weight of an almost colourless aqueous phase which contained sulphuric acid and had an acidity of 1.9 equivalents of $H^+/l$ and a COD value of 21,000 mg of $O_2/l$ remained; it contained about 25 g of $Na_2SO_4/l$, less than 0.3 g of cresolsulphonic acid/l and about 7 g of cresol/l.

After neutralising the aqueous phase with suspended calcium hydroxide, the COD value of the supernatant neutral solution was 16,000 mg of $O_2/l$; the BOD value was 7,100 mg of $O_2/l$ after 5 days, 15,800 mg of $O_2/l$ after 10 days and 16,000 mg of $O_2/l$ after 20 days. Furthermore, on dilution with water in a ratio of 1 : 4, the supernatant neutral aqueous solution showed only a weak harmful action against Pseudomonas fluorescenz and on dilution in a ratio of 1 : 8 it showed no further harmful action against Pseudomonas fluorescenz.

Thus, after neutralisation with suspended calcium hydroxide, the aqueous phase obtained after heating the acid effluent mixture and after separating off the organic phase is completely biodegradable.

EXAMPLE 8

1,000 parts by volume of the acid effluent mixture which was obtained according to Example 4 and had a COD value of 451,000 mg of $O_2/l$ were heated to 180° C/12 bars in an enamel kettle. After cooling and settling at about 25° C, 158 parts by weight of an organic phase and 828 parts by weight of an aqueous phase containing sulphuric acid were obtained; the properties of the phases obtained corresponded to those described in Example 7.

It was possible to reduce the cresol content of the aqueous phase containing sulphuric acid from 7 g/l to less than 1 g/l by means of steam distillation; the COD value was then only 2,000 mg of $O_2/l$.

EXAMPLE 9

A cascade consisting of four enamelled stirred kettles of equal size arranged in series was used in this example; the stirred kettles were connected by enamelled tubes and, by means of external heating with steam, kept at an internal temperature of 170° C and under an internal pressure of 9 bars. 1,000 parts by volume of the acid effluent mixture which was obtained according to Example 4 and had a COD value of 450,000 mg of $O_2/l$ were metered per hour into the cascade; the average residence time of the effluent in each kettle was about 4 hours After leaving the final cascade stage, the reaction mixture was cooled to about 35° C in a cooler and fed, via a reducing valve, into a settler, from which 155 parts by weight of the organic phase were withdrawn per hour under normal pressure.

The amount of the aqueous phase containing sulphuric acid which was obtained per hour from the settler was about 885 parts by weight; this phase contained 10 g of cresol/l and had a COD value of about 25,000 mg of $O_2/l$.

After neutralisation with suspended calcium hydroxide, this aqueous phase was fed continuously to a biological effluent treatment plant, where it could be processed without any difficulty.

What is claimed is:

1. A process for removing acids and potential acid-forming agents from the alkylphenol mixture obtained by reacting phenols with alkenes in the presence of sulfuric acid or sulfonic acids, for the treating effluent thereby obtained and for removal of organics from wash water obtained in the treatment of said effluent, comprising the steps of:
   (a) extracting the bulk of the acid constituents from the alkylphenol mixture by means of water;
   (b) treating the alkylphenol mixture with dilute aqueous alkali solution in an amount such that the alkali is insufficient to neutralize all the acid originally present in the alkylphenol mixture;
   (c) separating the alkylphenol mixture from the aqueous alkali solution;
   (d) combining the aqueous phases obtained in steps (a) and (b);
   (e) heating the combined aqueous phases to a temperature of 100° to 200° C;
   (f) separating off the organic phase obtained in step (e) and
   (g) discharging the aqueous phase.

2. A process according to claim 1 wherein process step (a) is so carried out that the residual acidity of the alkylphenol mixture after extraction with water is no greater than 0.005 equivalents of $H^+/kg$ of alkylate.

3. A process according to claim 1 wherein the extraction by water in process step (a) is carried out in the form of a multi-stage extraction.

4. A process according to claim 3 wherein the multi-stage extraction is carried out in counter-current fashion.

5. A process according to claim 1 wherein the alkali is an alkali metal carbonate or an alkali metal hydroxide.

6. A process according to claim 1 wherein the concentration of alkali is 1 to 10% by weight of alkali.

7. A process according to claim 6 wherein the concentration of alkali is 2 to 5% by weight of alkali.

8. A process according to claim 1 wherein the alkylphenol mixture has a residual alkalinity of at least 0.001 equivalents of $OH^-$/kg of mixture after the treatment with alkali in step (b).

9. A process according to claim 1 wherein the contact time between the alkylphenol mixture and alkali in step (b) is such that no alkylene is eliminated from the alkylphenol on heating the latter after step (b).

10. A process according to claim 1 wherein steps (a) and (b) are carried out at a temperature between 40° and 95° C.

11. A process according to claim 1 wherein steps (a) and (b) are carried out at up to 5 bars pressure.

12. A process according to claim 1 wherein step (e) is carried out at a temperature of between 140° and 190° C.

13. A process according to claim 1 wherein step (e) is carried out stepwise, continuously, isothermically or adiabatically.

14. A process according to claim 1 wherein all or part of the organic phase obtained in step (f) is recycled into steps (a) and (b).

15. A process according to claim 1 wherein all or part of the alkaline effluent produced from step (b) is used, in place of or in addition to water, in step (a).

16. A process according to claim 1 wherein the extraction with water according to step (a) is carried out in a plurality of stages with cross-currently flowing water.

* * * * *